US011497911B2

(12) United States Patent
Doran

(10) Patent No.: US 11,497,911 B2
(45) Date of Patent: Nov. 15, 2022

(54) ELECTRICALLY EVOKED RESPONSE (EER) STIMULATOR/AMPLIFIER COMBINATION

(71) Applicant: Diagnosys LLC, Lowell, MA (US)

(72) Inventor: Bruce Doran, Westford, MA (US)

(73) Assignee: Diagnosys LLC, Lowell, MA (US)

( * ) Notice: Subject to any disclaimer, the term of this patent is extended or adjusted under 35 U.S.C. 154(b) by 555 days.

(21) Appl. No.: 16/515,980

(22) Filed: Jul. 18, 2019

(65) Prior Publication Data
US 2020/0023185 A1    Jan. 23, 2020

Related U.S. Application Data

(60) Provisional application No. 62/700,055, filed on Jul. 18, 2018.

(51) Int. Cl.
| | |
|---|---|
| *A61N 1/36* | (2006.01) |
| *A61B 5/24* | (2021.01) |
| *A61B 5/398* | (2021.01) |
| *A61B 5/00* | (2006.01) |
| *A61N 1/08* | (2006.01) |
| *A61B 5/30* | (2021.01) |

(52) U.S. Cl.
CPC ............ *A61N 1/36046* (2013.01); *A61B 5/24* (2021.01); *A61B 5/398* (2021.01); *A61B 5/30* (2021.01); *A61B 5/4005* (2013.01); *A61N 1/08* (2013.01)

(58) Field of Classification Search
CPC .... A61N 1/36046; A61N 1/08; A61N 1/0404; A61B 5/24; A61B 5/398; A61B 5/30; A61B 5/4005; A61B 5/291; A61B 5/378
See application file for complete search history.

(56) References Cited

U.S. PATENT DOCUMENTS

| | | |
|---|---|---|
| 3,001,441 A | 9/1961 | Herbert |
| 3,012,472 A | 12/1961 | Feinberg et al. |
| 3,439,157 A | 4/1969 | Walter |

(Continued)

FOREIGN PATENT DOCUMENTS

| | | |
|---|---|---|
| CN | 101019760 | 8/2017 |
| EP | 0225072 | 6/1987 |

(Continued)

OTHER PUBLICATIONS

Potts et al. (The Electrically Evoked Response of the Visual System (EER), Investigative Ophthalmology & Visual Science, 7(3), 269-278) (Year: 1968).*

(Continued)

*Primary Examiner* — Jacqueline Cheng
*Assistant Examiner* — Tho Q Tran
(74) *Attorney, Agent, or Firm* — Pandiscio & Pandiscio

(57) ABSTRACT

Apparatus for ophthalmic electrophysiological testing, the apparatus comprising: an EER stimulator for providing an electrical stimulus to an eye so as to evoke an electrophysiological response, wherein the EER stimulator comprises a power source; an amplifier for receiving the electrophysiological response and measuring that response, wherein the amplifier is integrated with the EER stimulator; and at least one switch disposed between the power source and the amplifier for isolating the power source from the amplifier when the electrical stimulus is delivered to the eye.

30 Claims, 4 Drawing Sheets

(56) References Cited

U.S. PATENT DOCUMENTS

| | | | |
|---|---|---|---|
| 4,131,113 A | 12/1978 | Fender et al. | |
| 4,362,164 A | 12/1982 | Little et al. | |
| 4,618,230 A | 10/1986 | Ens et al. | |
| 4,740,072 A | 4/1988 | Griffin et al. | |
| 4,806,289 A | 2/1989 | Laursen et al. | |
| 4,874,237 A | 10/1989 | Cringle | |
| 4,910,090 A | 3/1990 | Kuhlman et al. | |
| 4,913,160 A * | 4/1990 | John | A61B 5/377 600/544 |
| 4,961,423 A * | 10/1990 | Canducci | A61N 1/365 607/20 |
| 5,141,305 A | 8/1992 | Young | |
| 5,943,116 A | 8/1999 | Zeimer | |
| 6,231,187 B1 | 5/2001 | Munoz et al. | |
| 8,810,482 B2 | 8/2014 | Abdollahi et al. | |
| 10,820,824 B2 | 11/2020 | Doran et al. | |
| 2003/0020875 A1 | 1/2003 | Sperling | |
| 2003/0149350 A1 | 8/2003 | Porciatti | |
| 2005/0245796 A1 | 11/2005 | Woods et al. | |
| 2006/0058857 A1 | 3/2006 | Tano et al. | |
| 2006/0095108 A1* | 5/2006 | Chowdhury | A61N 1/0543 607/141 |
| 2006/0184062 A1* | 8/2006 | Greenberg | A61N 1/36046 600/558 |
| 2006/0244915 A1 | 11/2006 | Clemons et al. | |
| 2008/0294066 A1 | 11/2008 | Hetling et al. | |
| 2010/0091242 A1 | 4/2010 | Baglini et al. | |
| 2010/0249532 A1 | 9/2010 | Maddess et al. | |
| 2010/0292999 A1 | 11/2010 | Verma | |
| 2011/0170064 A1 | 7/2011 | Taylor | |
| 2012/0069296 A1 | 3/2012 | Li et al. | |
| 2012/0143080 A1* | 6/2012 | Greenberg | A61N 1/36046 607/54 |
| 2013/0242077 A1 | 9/2013 | Lin et al. | |
| 2013/0278899 A1 | 10/2013 | Waldorf et al. | |
| 2013/0285886 A1 | 10/2013 | Pombo et al. | |
| 2014/0128763 A1 | 5/2014 | Fadem | |
| 2014/0333898 A1 | 11/2014 | Boate et al. | |
| 2015/0029463 A1 | 1/2015 | Hetling et al. | |
| 2015/0191240 A1 | 7/2015 | Burchard | |
| 2015/0313467 A1 | 11/2015 | Sakai et al. | |
| 2017/0014074 A1 | 1/2017 | Etzkorn et al. | |
| 2017/0042441 A1 | 2/2017 | Doran et al. | |
| 2017/0127970 A1 | 5/2017 | Doran et al. | |
| 2018/0236230 A1* | 8/2018 | Pilly | A61B 5/24 |

FOREIGN PATENT DOCUMENTS

| | | |
|---|---|---|
| EP | 2314201 | 4/2011 |
| JP | 2011-087609 | 5/2011 |
| WO | WO 2001/078586 | 10/2001 |
| WO | WO 2005/002420 | 1/2005 |
| WO | WO 2008/024222 | 2/2008 |
| WO | WO 2008/070683 | 6/2008 |
| WO | WO 2010/066420 | 6/2010 |
| WO | WO 2015/191240 | 12/2015 |
| WO | WO 2016/162796 | 10/2016 |

OTHER PUBLICATIONS

Burr-Brown Products From Texas Instruments, Single-Supply Differential Amplifier, Texas Instruments Incorporated, 2001 pp. 1-18.

ColorDome LabCradle: Advanced Animal ERG Testing, Diagnosys, LLC, 2017.

EER Module: Electrically evoked response stimulator, Diagnosys LLC, 2018.

Electrically Evoked Response: Note, Diagnosys, LLC, 2018, pp. 1-8.

Frishman, Laura et al., ISCEV extended protocol for the photopic negative response (PhNR) of the full-field electroretinogram, Doc Ophthalmol, vol. 136, No. 3, 2018, pp. 207-211.

Heath, Janet, Amplifiers: What do rail-to-rail and single supply mean?, Analog IC Tips, 2017, https://www.analogictips.com/amplifiers-rail-to-rail-single-supply-mean/.

Luo, Xunda et al. Retinal Pathway Origins of the Pattern Electroretinogram (PERG), Investigative Ophthalmology & Visual Science, vol. 52, No. 12, 2011, pp. 8571-8584.

Matsumoto, Celso S. et al., Pattern Visual Evoked Potentials Elicited by Organic Electroluminescence Screen, BioMed Research International, vol. 2014, pp. 1-6.

Viswanathan, Suresh et al. The Uniform Field and Pattern ERG in Macaques With Experimental Glaucoma: Removal of Spiking Activity, Investigative Ophthalmology & Visual Science, vol. 41, No. 9, 2000, pp. 2797-2810.

Blanchard, P. et al., Using ESD Diodes as Voltage Clamps, Analog Dialogue 49-10, Oct. 2015, pp. 1-3.

* cited by examiner

ERG (ELECTRORETINOGRAPHY) TESTING

CONVENTIONAL EER TESTING, AND NOVEL ERG TESTING USING EER TEST APPARATUS
(AND NOVEL STIMULATOR/AMPLIFIER COMBINATION)

ELECTRICALLY EVOKED RESPONSE (EER) STIMULATOR/AMPLIFIER COMBINATION

REFERENCE TO PENDING PRIOR PATENT APPLICATION

This patent application claims benefit of pending prior U.S. Provisional Patent Application Ser. No. 62/700,055, filed Jul. 18, 2018 by Diagnosys LLC and Bruce Doran for NOVEL EER STIMULATOR, which patent application is hereby incorporated herein by reference.

BACKGROUND OF THE INVENTION

Ophthalmic electrophysiology relates to electrophysiological measures of visual function. Ophthalmic electrophysiology is the only objective measure of visual function—all other ophthalmic diagnostics are either subjective or a measure of structure and not function.

One type of ophthalmic electrophysiology is electroretinography (ERG). ERG measures the electrical responses of various cell types in the retina, including the photoreceptors, inner retinal cells, and the ganglion cells. With ERG, flashes of light or moving patterns of light are used to stimulate the eye, and the resulting electrical response of the retina is detected from electrodes applied to the cornea.

Another type of ophthalmic electrophysiology is visual evoked potential (VEP). With VEP, light is used to stimulate the eye, and the resulting electrical response of the visual cortex is detected using electrodes applied to the scalp above the visual cortex.

Still another type of ophthalmic electrophysiology is electrically evoked response (EER). With EER, the eye is stimulated electrically instead of optically, by introducing a small shaped pulse of current to the cornea. The resulting response is measured from the visual cortex via skin electrodes placed on the scalp.

EER is useful in determining the integrity of the visual system in circumstances where light cannot be used as a stimulus. It is most commonly used to assess salvageability in trauma cases, when the eye is filled with blood.

EER is also used to assess the integrity of remaining visual system function in no-light-perception patients who lack intact photoreceptors. Patients who lack photoreceptors may be candidates for developing therapies that can regenerate them. Unless post-retinal visual pathways remain intact, however, regeneration of the photoreceptors will not restore vision. Candidates for such therapies therefore need to be screened to exclude patients who will not benefit from treatment.

EER stimulation is not new to the field of ophthalmic electrophysiology, and electrical stimulators exist that can elicit the desired physiological response. Unfortunately, these electrical stimulators are stand-alone pieces of equipment which are separate from the amplifiers and data acquisition systems used to measure the electrical response from the patient. Consequently, existing electrical stimulators are hard to set up, difficult to standardize, and potentially hazardous to the patient.

SUMMARY OF THE INVENTION

The present invention provides a novel EER stimulator which avoids these shortcomings by being incorporated into a highly sensitive, highly linear 5-channel-32-bit medical amplifier. The novel EER stimulator/amplifier combination uses only standard amplifier connections to the patient to both deliver the electrical stimulus to the patient and to measure the response from the patient, enhancing ease-of-use, improving accuracy, and avoiding any possible harm to the patient that might result from the use of two unintegrated systems (i.e., stimulator and amplifier) with separate ground and control connections.

In addition to recording EER, the novel EER stimulator/amplifier combination is also capable of measuring an ERG response to an EER stimulus so as to assess retinal function. This capability is unique to the novel EER stimulator/amplifier combination of the present invention. More particularly, the EER system delivers the EER stimulus to the eye via a corneal electrode. In conventional systems, a second corneal electrode is required to measure the ERG response. Even if such an electrode were employed, however, the EER stimulus would be clipped by the input protection diodes of the amplifier reading the ERG response. These input protection diodes limit any voltage applied to their inputs to a value less than that required for effective EER stimulation. Consequently, the ERG response to a full EER stimulus cannot be measured using conventional equipment.

With the novel EER stimulator/amplifier combination of the present invention, the EER stimulator is isolated from the amplifier during EER stimulation by a fast-acting computer-controlled switch that can restore the amplifier connection as soon as the EER stimulus is complete. As a result, the full EER stimulus can be delivered to the cornea without amplifier clipping and, significantly, the same corneal electrode which is used to deliver the EER stimulation can also be used to detect the ERG response from the cornea. This arrangement also eliminates the need for a second corneal electrode in the same eye. In this way, the novel EER stimulator/amplifier combination of the present invention can measure both the retinal and the cortical response to an EER stimulus (i.e., the ERG and EER responses to an EER stimulus). This is not possible with conventional EER and ERG systems.

The integration of the EER stimulator with the data acquisition amplifier enhances both the safety and the accuracy of the EER stimulus. For example, it is possible to control the EER stimulus so that the current produced by the EER stimulator is completely symmetrical about the resting baseline patient voltage. This is important because otherwise the EER stimulator would impose, with each pulse, a DC potential across the patient which could ultimately result in plating electrode material into the eye. In order to ensure proper pulse symmetry, the current source should be monitored as it is applied to the patient. This is not possible unless the amplifier and the EER stimulator are closely integrated.

Another safety feature of this integration is that it permits the stimulus current to be measured both before and during its application to the patient. The hardware integrity can be checked prior to every pulse, and then confirmed during delivery. Measurement of the current pulse during stimulation confirms not only that the correct current is being delivered, but also verifies the integrity of the connections between device and patient, resulting in 100% verification that the correct stimulus has been applied.

Although the EER stimulus currents are applied only briefly to the patient, they exceed (by a large factor) the steady state leakage current allowed to be applied to a patient under ordinary conditions. For this reason it is important not only to control precisely the duration and amplitude of the applied currents, but also to ensure that the currents can neither be accidentally applied nor unintentionally be allowed to remain on. The integration of stimulator and amplifier facilitates this by making it practical to turn the power to the stimulator system completely off when it is not being used, and to limit the ground return current to a steady-state safe value (less than 10 µA) at all times except during the stimulus pulse.

In one preferred form of the present invention, there is provided apparatus for ophthalmic electrophysiological testing, the apparatus comprising:
an EER stimulator for providing an electrical stimulus to an eye so as to evoke an electrophysiological response, wherein the EER stimulator comprises a power source;
an amplifier for receiving and measuring the electrophysiological response, wherein the amplifier is integrated with the EER stimulator; and
at least one switch disposed between the power source and the amplifier for isolating the power source from the amplifier when the electrical stimulus is delivered to the eye.

In another preferred form of the present invention, there is provided a method for ophthalmic electrophysiological testing, the method comprising:
providing apparatus comprising:
an EER stimulator for providing an electrical stimulus to an eye so as to evoke an electrophysiological response, wherein the EER stimulator comprises a power source;
an amplifier for receiving and measuring the electrophysiological response, wherein the amplifier is integrated with the EER stimulator; and
at least one switch disposed between the power source and the amplifier for isolating the power source from the amplifier when the electrical stimulus is delivered to the eye;
electrically isolating the power source from the amplifier;
delivering an electrical stimulus to the eye using a first electrode connected to the EER stimulator;
electrically isolating the power source from the first electrode and electrically connecting the first electrode to the amplifier; and
capturing an electrophysiological response via the first electrode and using the amplifier to measure the electrophysiological response.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
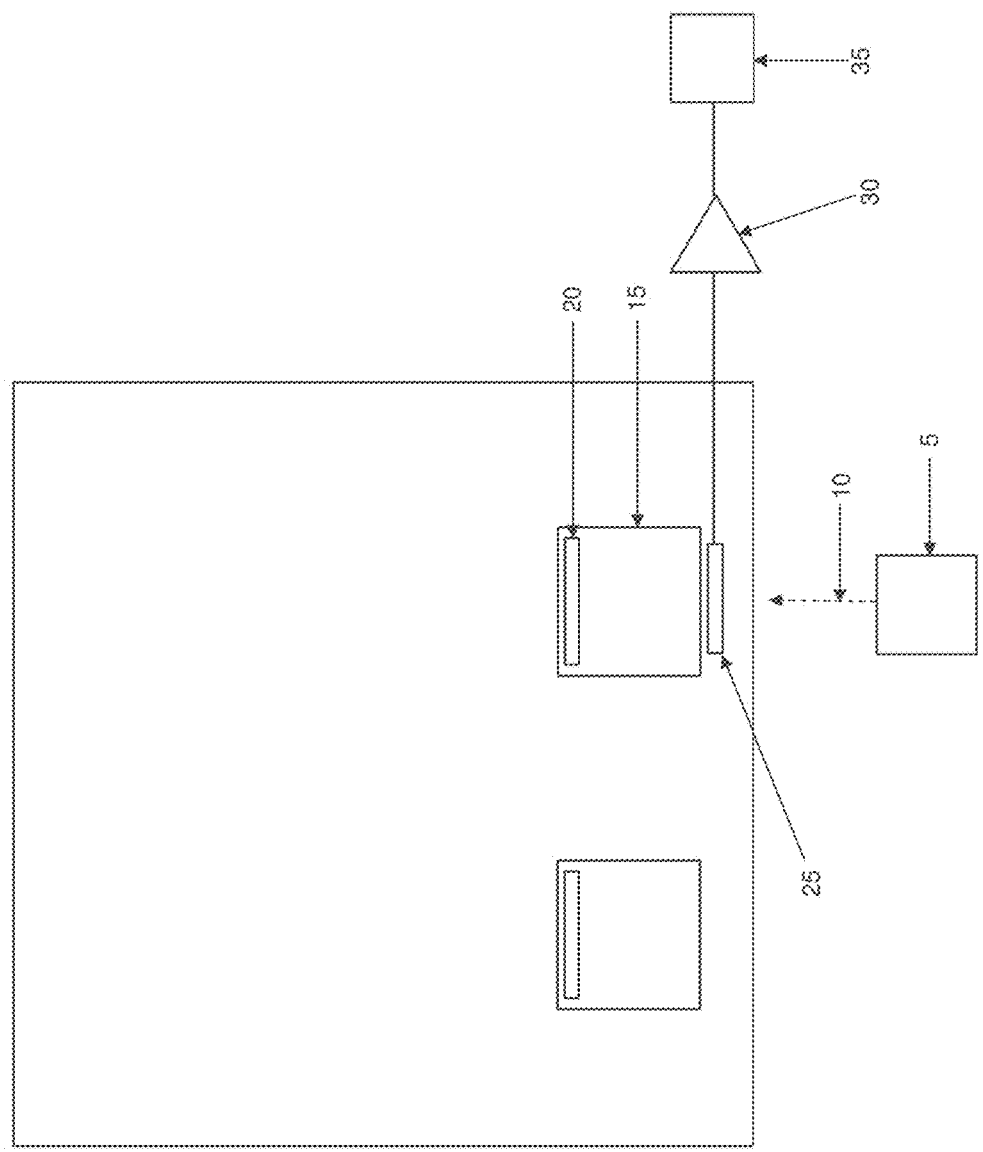
FIG. 1 is a schematic view showing a prior art ERG system.

The present invention provides a novel EER stimulator which avoids the shortcomings associated with the prior art by being incorporated into a highly sensitive, highly linear 5-channel-32-bit medical amplifier. The novel EER stimulator/amplifier combination uses only standard amplifier connections to the patient to both deliver the electrical stimulus to the patient and to measure the response from the patient, enhancing ease-of-use, improving accuracy, and avoiding any possible harm to the patient that might result from the use of two unintegrated systems (i.e., stimulator and amplifier) with separate ground and control connections.

In addition to recording EER, the novel EER stimulator/amplifier combination is also capable of measuring an ERG response to an EER stimulus so as to assess retinal function. This capability is unique to the novel EER stimulator/amplifier combination of the present invention. More particularly, the EER system delivers the EER stimulus to the eye via a corneal electrode. In conventional systems, a second corneal electrode is required to measure the ERG response. Even if such an electrode were employed, however, the EER stimulus would be clipped by the input protection diodes of the amplifier reading the ERG response. These input protection diodes limit any voltage applied to their inputs to a value less than that required for effective EER stimulation. Consequently, the ERG response to a full EER stimulus cannot be measured using conventional equipment.

With the novel EER stimulator/amplifier combination of the present invention, the EER stimulator is isolated from the amplifier during EER stimulation by a fast-acting computer-controlled switch that can restore the amplifier connection as soon as the EER stimulus is complete. As a result, the full EER stimulus can be delivered to the cornea without amplifier clipping and, significantly, the same corneal electrode which is used to deliver the EER stimulation can also be used to detect the ERG response from the cornea. This arrangement also eliminates the need for a second corneal electrode in the same eye. In this way, the novel EER stimulator/amplifier combination of the present invention can measure both the retinal and the cortical response to an EER stimulus (i.e., the ERG and EER responses to an EER stimulus). This is not possible with conventional EER and ERG systems.

The integration of the EER stimulator with the data acquisition amplifier enhances both the safety and the accuracy of the EER stimulus. For example, it is possible to control the EER stimulus so that the current produced by the EER stimulator is completely symmetrical about the resting baseline patient voltage. This is important because otherwise the EER stimulator would impose, with each pulse, a DC potential across the patient which could ultimately result in plating electrode material into the eye. In order to ensure proper pulse symmetry, the current source should be monitored as it is applied to the patient. This is not possible unless the amplifier and the EER stimulator are closely integrated.

Another safety feature of this integration is that it permits the stimulus current to be measured both before and during its application to the patient. The hardware integrity can be checked prior to every pulse, and then confirmed during delivery. Measurement of the current pulse during stimulation confirms not only that the correct current is being delivered, but also verifies the integrity of the connections between device and patient, resulting in 100% verification that the correct stimulus has been applied.

Although the EER stimulus currents are applied only briefly to the patient, they exceed (by a large factor) the steady state leakage current allowed to be applied to a patient under ordinary conditions. For this reason it is important not only to control precisely the duration and amplitude of the applied currents, but also to ensure that the currents can neither be accidentally applied nor unintentionally be allowed to remain on. The integration of stimulator and amplifier facilitates this by making it practical to turn the power to the stimulator system completely off when it is not being used, and to limit the ground return current to a steady-state safe value (less than 10 µA) at all times except during the stimulus pulse.

FIG. 1 shows a conventional ERG system. In such a system, a stimulator 5 drives a light source or a light pattern 10 so as to cause light to fall on an eye 15, whereby to induce an electrical response from the retina 20 of eye 15. This ERG electrical response is detected by a corneal electrode 25, measured by an amplifier 30 and then processed by a processor 35 so as to identify electrophysiological measures of visual function.

Figure 2:
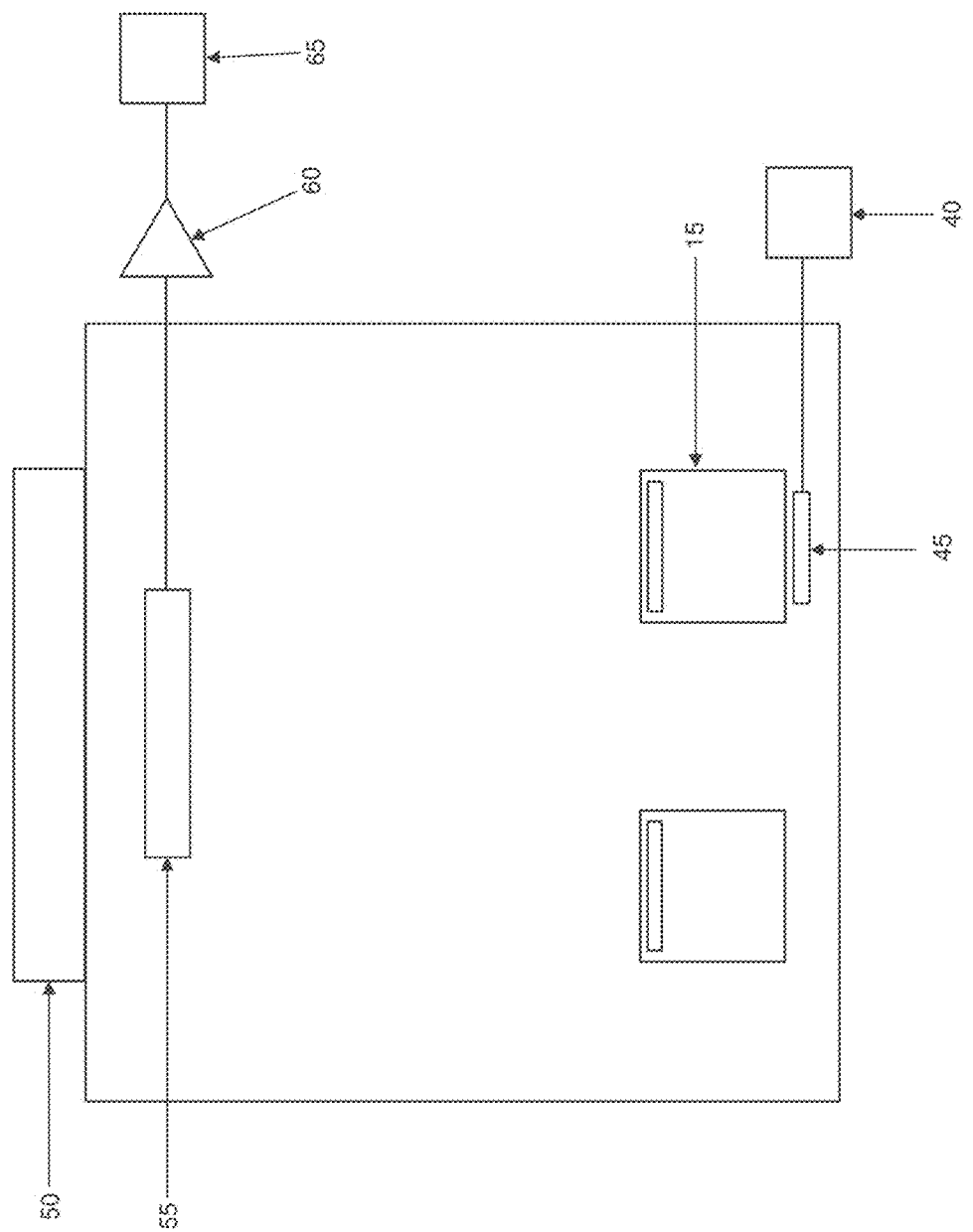
FIG. 2 is a schematic view showing a prior art EER system.

FIG. 2 shows a conventional EER system. In such a system, a stimulator 40 provides an electrical signal to a corneal electrode 45 positioned against an eye 15, whereby to induce an electrical response from the visual cortex 50. This EER electrical response is detected by scalp electrodes 55, measured by an amplifier 60 and then processed by a processor 65 so as to identify electrophysiological measures of visual function.

Figure 3:
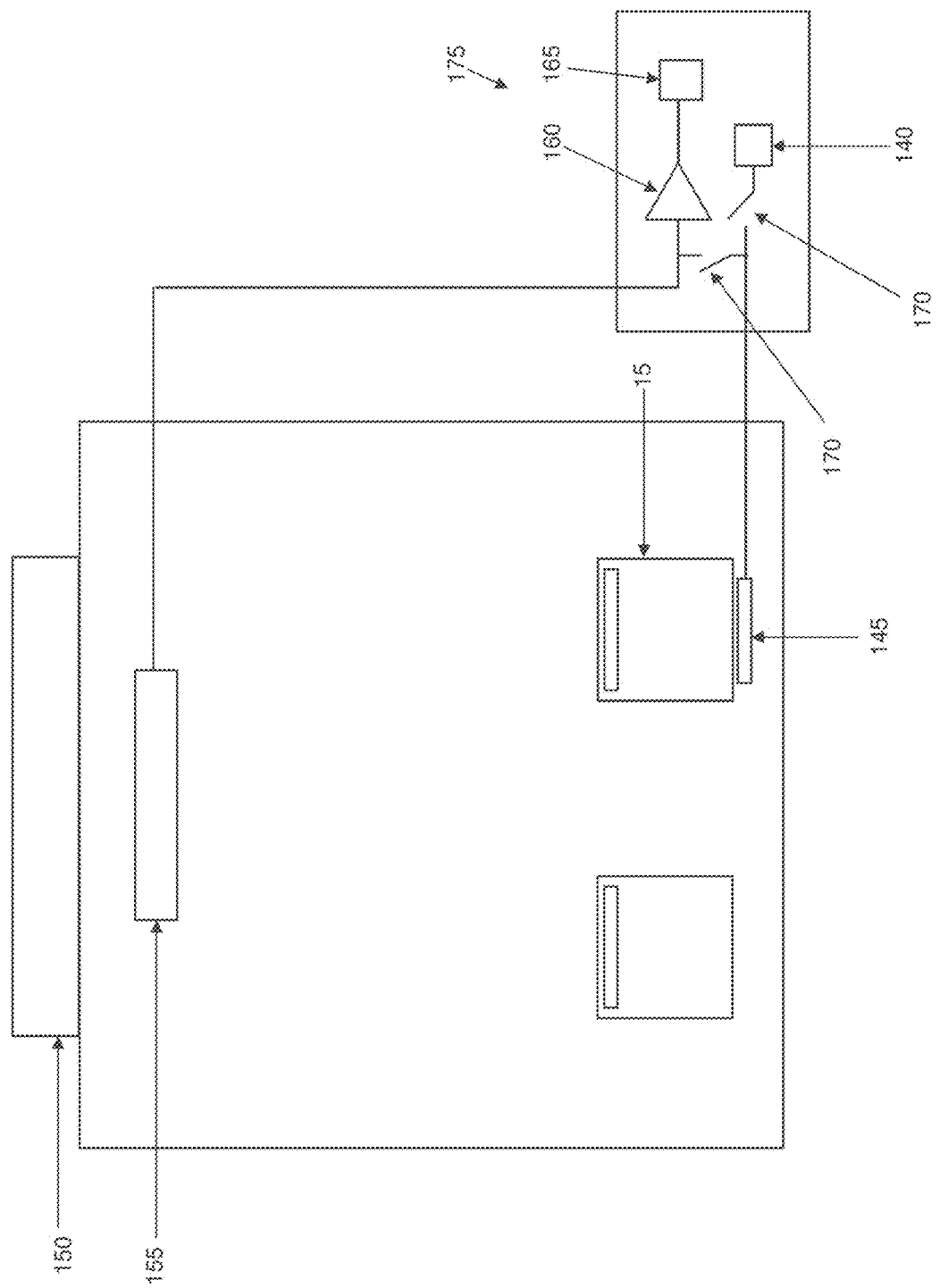
FIG. 3 is a schematic view showing a novel system formed in accordance with the present invention which can be used for conventional EER testing, and novel ERG testing using novel EER test apparatus (which includes a novel stimulator/amplifier combination)

FIG. 3 shows a novel EER system formed in accordance with the present invention. In the novel EER system of the present invention, a stimulator 140 provides an electrical signal to a corneal electrode 145 positioned against an eye 15, whereby to induce an electrical response from the visual cortex 150. This EER electrical response is detected by scalp electrodes 155, measured by an amplifier 160 and then processed by a processor 165 so as to identify electrophysiological measures of visual function. In one preferred form of the invention, three scalp electrodes 155 are utilized.

In accordance with the present invention, the ERG electrical response to an EER stimulus may also be detected by corneal electrode 145. The ERG electrical response detected by corneal electrode 145 is measured by amplifier 160 and then processed by a processor 165 so as to identify electrophysiological measures of visual function. In order to prevent the EER stimulus from being clipped by the input protection diodes of the amplifier reading the ERG response, a fast-acting computer-controlled switch 170 can isolate the corneal electrode from the amplifier connection during application of the EER stimulation, and can restore the amplifier connection as soon as the EER stimulation is complete. In one preferred form of the invention, fast-acting computer-controlled switch 170 comprises a switch 170 disposed between the stimulator 140 and the corneal electrode 145, and a switch 170 disposed between the corneal electrode 145 and the amplifier 160. As a result, the full EER stimulus can be delivered to the cornea without amplifier clipping and, significantly, the same corneal electrode which is used to deliver the EER stimulation can also be used to detect the ERG response from the cornea.

It will be appreciated that the novel EER system of FIG. 3 comprises a novel electrically evoked response (EER) stimulator/amplifier combination 175.

Figure 4:
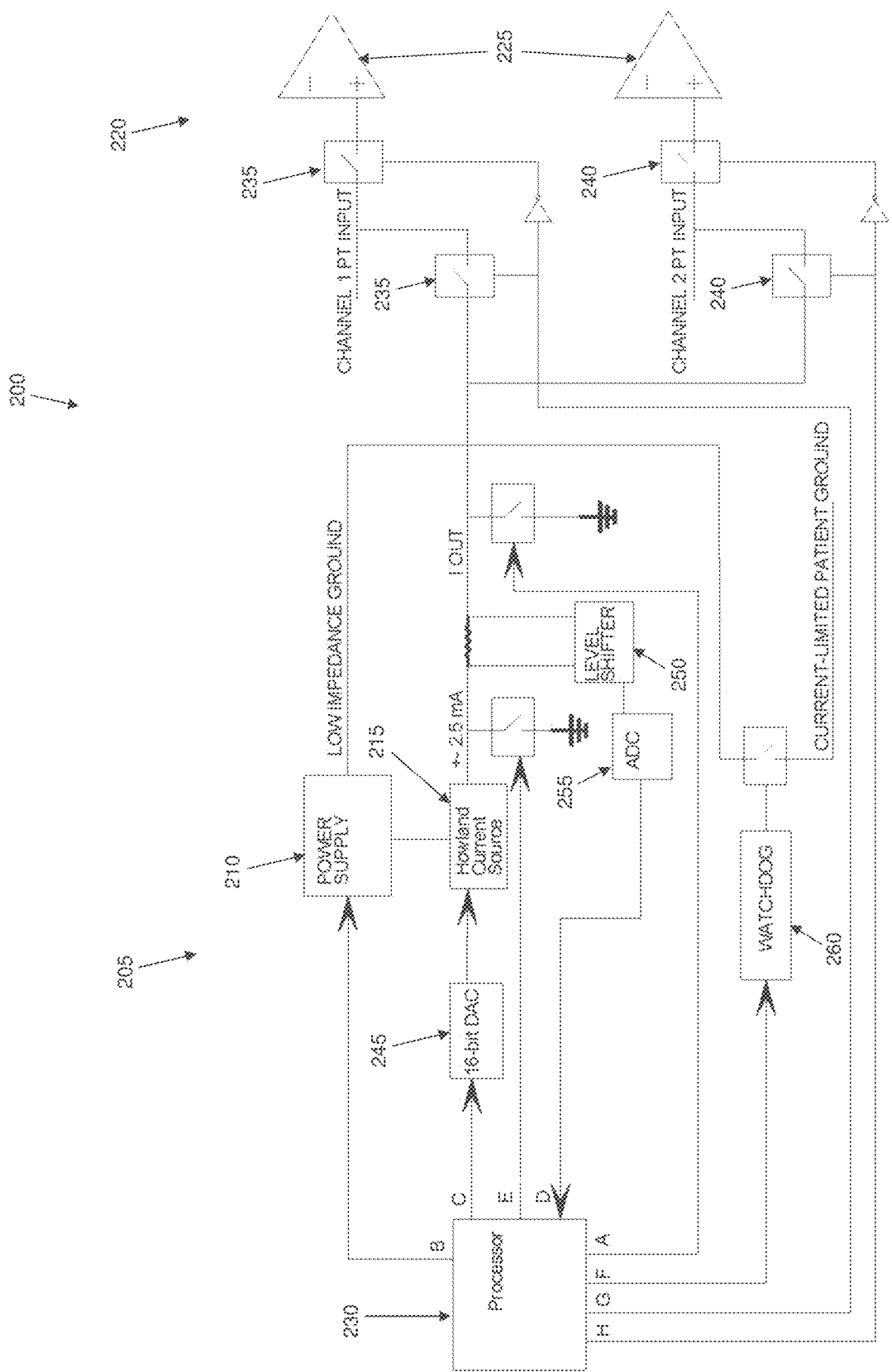
FIG. 4 is a schematic view showing an exemplary system formed in accordance with the present invention which can be used for conventional EER testing, and novel ERG testing using novel EER test apparatus (which includes a novel stimulator/amplifier combination).

FIG. 4 shows an exemplary novel electrically evoked response (EER) stimulator/amplifier combination 200 formed in accordance with the present invention. More particularly, exemplary novel electrically evoked response (EER) stimulator/amplifier combination 200 generally comprises (i) a stimulator 205 which generally comprises a power supply 210 and a Howland current source 215, (ii) an amplifier 220 which generally comprises a pair of operational amplifiers 225, and (iii) a CPU 230. Stimulator 205 is connected to amplifier 220 via a pair of switches 235 and a pair of switches 240. CPU 230 is connected to the Howland current source via a 16-bit DAC 245. Amplifier 220 is connected to CPU 230 via a Level Shifter 250 and an Analog-to-Digital Converter (ADC) 255. CPU 230 is connected to a Watchdog 260 which essentially comprises a timer which resets periodically and which shuts down the system if it does not receive its periodic reset (i.e., by connecting the low impedance ground of the power supply to the current-limited patient ground).

The exemplary novel electrically evoked response (EER) stimulator/amplifier combination 200 shown in FIG. 4 is intended to operate as follows:

1. CPU output (Control A) and current source (Control E) are grounded.
2. The EER power supply (Control B) is turned on.
3. The ADC is zeroed.
4. The current source (Control E) is ungrounded.
5. Positive DAC current (Bus C) is written and ADC current (Bus D) is read to confirm positive current is correct.
6. Negative DAC current (Bus C) is written and ADC current (Bus D) is read to confirm negative current is correct.
7. DAC current (Bus C) is written to zero.
8. Strobing of low impedance ground watchdog (Control E) begins.
9. There is a 2 millisecond delay.
10. The Channel 1 or Channel 2 EER output switch is turned on and the amplifier ADC is disconnected from output (Control G or H).
11. Output (Control A) is ungrounded.
12. Current pulses are written as directed by protocol, finish by writing zero current to DAC (Control C).
13. The EER current is disconnected from output pin (Control G or H).
14. The EER output (Control A) and current source (Control E) are grounded.
15. Strobing of low impedance ground watchdog (Control E) is discontinued.
16. The power supply (Control B) is turned off.

MODIFICATIONS OF THE PREFERRED EMBODIMENTS

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:
1. Apparatus for ophthalmic electrophysiological testing, the apparatus comprising:
an electrically evoked response (EER) stimulator for providing an electrical stimulus to an eye so as to evoke an electrophysiological response, wherein a first electrode is connected to the EER stimulator for (i) delivering the electrical stimulus to the eye, and (ii) recording an electrophysiological response from the eye, wherein the EER stimulator comprises a power source;
an amplifier for receiving and measuring the recorded electrophysiological response from the eye, wherein the amplifier is integrated with the EER stimulator; and
at least one switch disposed between the power source and the amplifier for isolating the power source from the amplifier when the electrical stimulus is delivered to the eye by the first electrode.

2. Apparatus according to claim 1 wherein the first electrode comprises a corneal electrode.

3. Apparatus according to claim 1 wherein the at least one switch is a computer-controlled switch.

4. Apparatus according to claim 3 wherein the at least one switch comprises a first switch and a second switch.

5. Apparatus according to claim 4 wherein the first switch is disposed between the power source and the first electrode, and the second switch is disposed between the first electrode and the amplifier.

6. Apparatus according to claim 1 wherein the EER stimulator comprises a watchdog circuit for monitoring the electrical stimulus provided to an eye.

7. Apparatus according to claim 1 wherein the electrical stimulus is symmetrical about a baseline voltage.

8. Apparatus according to claim 1 wherein the amplifier is a linear 5-channel-32-bit medical amplifier.

9. A method for ophthalmic electrophysiological testing, the method comprising:
providing apparatus comprising:
an electrically evoked response (EER) stimulator for providing an electrical stimulus to an eye so as to evoke an electrophysiological response, wherein a first electrode is connected to the EER stimulator for (i) delivering the electrical stimulus to the eye, and (ii) recording an electrophysiological response from the eye, wherein the EER stimulator comprises a power source;
an amplifier for receiving and measuring the recorded electrophysiological response from the eye, wherein the amplifier is integrated with the EER stimulator; and
at least one switch disposed between the power source and the amplifier for isolating the power source from the amplifier when the electrical stimulus is delivered to the eye by the first electrode;
electrically isolating the power source from the amplifier;
delivering an electrical stimulus to the eye using the first electrode;
electrically isolating the power source from the first electrode and electrically connecting the first electrode to the amplifier; and
capturing an electrophysiological response via the first electrode and using the amplifier to measure the electrophysiological response.

10. A method according to claim 9 wherein the first electrode comprises a corneal electrode.

11. A method according to claim 9 further comprising:
capturing an electrophysiological response via at least one second electrode connected to the amplifier.

12. A method according to claim 11 wherein the at least one second electrode captures an electrophysiological response from the visual cortex.

13. A method according to claim 12 wherein the at least one second electrode is a scalp electrode.

14. A method according to claim 12 wherein the at least one second electrode comprises three scalp electrodes.

15. A method according to claim 9 wherein the at least one switch is a computer-controlled switch.

16. A method according to claim 15 wherein the at least one switch comprises a first switch and a second switch.

17. A method according to claim 16 wherein the first switch is disposed between the power source and the first electrode, and the second switch is disposed between the first electrode and the amplifier.

18. A method according to claim 9 wherein the EER stimulator comprises a watchdog circuit for monitoring the electrical stimulus provided to an eye.

19. A method according to claim 9 wherein the electrical stimulus is symmetrical about a baseline voltage.

20. A method according to claim 9 wherein the amplifier is a highly linear 5-channel-32-bit medical amplifier.

21. Apparatus for ophthalmic electrophysiological testing, the apparatus comprising:
an electrically evoked response (EER) stimulator for providing an electrical stimulus to an eye so as to evoke an electrophysiological response, wherein the EER stimulator comprises a power source;
an amplifier for receiving and measuring the electrophysiological response, wherein the amplifier is integrated with the EER stimulator; and
at least one switch disposed between the power source and the amplifier for isolating the power source from the amplifier when the electrical stimulus is delivered to the eye;
wherein the at least one switch is a computer-controlled switch; and
wherein the at least one switch comprises (i) a switch disposed between the power source and a first electrode, and (ii) a switch disposed between the first electrode and the amplifier.

22. Apparatus according to claim 21 wherein at least one second electrode is connected to the amplifier for receiving an electrophysiological response from the visual cortex.

23. Apparatus according to claim 22 wherein the at least one second electrode is a scalp electrode.

24. Apparatus according to claim 22 wherein the at least one second electrode comprises three scalp electrodes.

25. Apparatus according to claim 21 wherein the first electrode is connected to the EER stimulator for delivering the electrical stimulus to the eye and for receiving the electrophysiological response from the eye.

26. Apparatus according to claim 21 wherein the first electrode comprises a corneal electrode.

27. Apparatus according to claim 21 wherein the EER stimulator comprises a watchdog circuit for monitoring the electrical stimulus provided to an eye.

28. Apparatus according to claim 21 wherein the electrical stimulus is symmetrical about a baseline voltage.

29. Apparatus according to claim 21 wherein the amplifier is a linear 5-channel-32-bit medical amplifier.

30. A method for ophthalmic electrophysiological testing, the method comprising:
providing apparatus comprising:
an electrically evoked response (EER) stimulator for providing an electrical stimulus to an eye so as to evoke an electrophysiological response, wherein the EER stimulator comprises a power source;
an amplifier for receiving and measuring the electrophysiological response, wherein the amplifier is integrated with the EER stimulator; and
at least one switch disposed between the power source and the amplifier for isolating the power source from the amplifier when the electrical stimulus is delivered to the eye;
wherein the at least one switch is a computer- controlled switch;
wherein the at least one switch comprises two switches;
wherein the at least one switch comprises (i) a switch disposed between the power source and a first electrode connected to the EER stimulator, and (ii) a switch disposed between the first electrode and the amplifier;

electrically isolating the power source from the amplifier;

delivering an electrical stimulus to the eye using the first electrode;

electrically isolating the power source from the first electrode and electrically connecting the first electrode to the amplifier; and capturing an electrophysiological response via the first electrode and using the amplifier to measure the electrophysiological response.

* * * * *